(12) United States Patent
Schumer et al.

(10) Patent No.: US 6,565,585 B2
(45) Date of Patent: May 20, 2003

(54) CORNEAL SURGICAL APPARATUS

(75) Inventors: James D. Schumer, Mansfield, OH (US); Minoru Toh, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/886,489

(22) Filed: Jun. 22, 2001

(65) Prior Publication Data

US 2002/0198553 A1 Dec. 26, 2002

(51) Int. Cl.[7] ................................................ A61F 5/00
(52) U.S. Cl. ...................................................... 606/166
(58) Field of Search ........................... 606/1, 166, 167, 606/169, 180, 107, 178, 161, 172, 67

(56) References Cited

U.S. PATENT DOCUMENTS

| | | | |
|---|---|---|---|
| 3,714,819 A | | 2/1973 | Webb ............................... 73/80 |
| 4,747,296 A | | 5/1988 | Feldon et al. ..................... 73/4 |
| 5,134,991 A | * | 8/1992 | Hustead ....................... 128/858 |
| 5,997,559 A | * | 12/1999 | Ziemer ......................... 606/166 |
| 6,045,562 A | * | 4/2000 | Amano et al. ............... 606/166 |
| 6,059,805 A | | 5/2000 | Sugimura et al. ........... 606/166 |
| 6,071,293 A | * | 6/2000 | Krumeich .................... 606/166 |
| 6,132,446 A | * | 10/2000 | Hellenkamp et al. ....... 606/166 |
| 6,277,134 B1 | * | 8/2001 | Amano et al. ............... 606/166 |
| 6,296,650 B1 | * | 10/2001 | Carriazo ...................... 606/166 |
| 6,312,440 B1 | * | 11/2001 | Hood et al. .................. 606/166 |

FOREIGN PATENT DOCUMENTS

JP        8-107        1/1996

* cited by examiner

*Primary Examiner*—Kevin T. Truong
*Assistant Examiner*—Victor X Nguyen
(74) *Attorney, Agent, or Firm*—Finnegan, Henderson, Farabow, Garrett & Dunner LLP

(57) ABSTRACT

A corneal surgical apparatus includes: a suction ring to be fixed to a patient's eye, the suction ring having an opening; a suction unit which absorbs air in a space defined between the patient's eye and the suction ring, and which variably sets a suction pressure; a setting unit which sets a desired ocular pressure for the patient eye during surgery, the desired ocular pressure having a predetermined tolerable range; an input unit which inputs a measured ocular pressure of the patient's eye; a controller which controls operation of the suction unit based on the inputted ocular pressure to obtain the set ocular pressure, and which is connected to the suction unit, the setting unit and the input unit.

12 Claims, 7 Drawing Sheets

CORNEAL SURGICAL APPARATUS

BACKGROUND OF THE INVENTION

1. Field of the Invention

The present invention relates to a corneal surgical apparatus for incising the cornea of an eye of a patient in a layered fashion at the time of a keratorefrative surgery or the like.

2. Description of the Related Art

In recent years, attention has been focused on a LASIK surgery (laser in situ keratomileusis) for the keratorefractive surgery wherein a flap is formed by incising a corneal portion with a thickness of about 0.15 mm from the corneal epithelium to the corneal stroma with a part of the cornea remaining connected like a hinge, ablating the corneal stroma in a refractive correction amount by an excimer laser light, and returning the flap to its original position. In the LASIK surgery, a corneal surgical apparatus called a microkeratome is used for incising the cornea in a layered fashion.

As a corneal surgical apparatus, one comprising a suction ring to be vacuum-fixed to the conjunctiva surrounding the cornea, a cornea applanating plate for applanating the cornea flatly, and a blade movable toward the hinge while oscillating laterally so as to incise the flattened cornea into a layer with a substantially uniform thickness, is known.

When the suction ring is vacuum-fixed to a patient's eye prior to flap formation, the ocular pressure (ocular tension) of the patient's eye is increased in a manner which varies from patient to patient. Further, since suction pressure (vacuum pressure) applied to a space between the patient's eye and the suction ring is constant, the thickness of the flap varies depending on the ocular pressure. In general, as the ocular pressure is higher, the flap is thicker. If the flap is too thick, corneal weakening or "Ectasia", i.e. where due to weakening the cornea progressively changes over time, is likely to appears. On the other hand, if the ocular pressure is too low, a thin flap or a button hole may be formed through the flap, which hinders the formation of an appropriate flap.

SUMMARY OF THE INVENTION

Consistent with the present invention, a corneal surgical apparatus is provided that avoids problems associated with prior corneal surgical apparatuses as discussed herein above.

In one aspect, a corneal surgical apparatus comprises a suction ring to be mounted on a patient's eye, a suction unit which applies a suction pressure to a space defined between the patient's eye and the mounted suction ring, a setting unit which sets a desired ocular pressure for the patient's eye, an input unit which inputs a measured ocular pressure of the patient's eye, and a controller which controls the suction pressure to be applied by the suction unit based on comparison between the inputted ocular pressure and the set ocular pressure.

In another aspect, a corneal surgical apparatus comprises a suction ring to be mounted on a patient's eye, a suction unit which applies a suction pressure to a space defined between the patient's eye and the mounted suction ring, a setting unit which sets a desired ocular pressure for the patient's eye, an input unit which inputs a measured ocular pressure of the patient's eye, a pressure sensor which detects the suction pressure applied by the suction unit, a memory which stores the suction pressure detected when the inputted ocular pressure is identical to the set ocular pressure, and a controller which controls the suction pressure to be applied by the suction unit based on comparison between detected suction pressure and the stored suction pressure.

In yet another aspect, a corneal surgical apparatus comprises a suction ring to be mounted on a patient's eye, a suction unit which applies a suction pressure to a space defined between the patient's eye and the mounted suction ring, a setting unit which sets a desired ocular pressure for the patient's eye, an input unit which inputs a measured ocular pressure of the patient's eye, a pressure sensor which detects the suction pressure applied by the suction unit, a memory which stores a plurality of the inputted ocular pressures measured when different suction pressures are applied, and the detected suction pressures when those ocular pressures are respectively measured, in relation to each other, and a controller which calculates the suction pressure corresponding to the set ocular pressure based on plural sets of the ocular pressures and suction pressures stored in the memory, stores the calculated suction pressure in the memory, and controls the suction pressure to be applied by the suction unit based on comparison between detected suction pressure and the calculated and stored suction pressure.

Both the foregoing general description and the following detailed description are exemplary and are intended to provide further explanation of the invention as claimed.

DESCRIPTION OF THE PREFERRED EMBODIMENT

Figure 1:
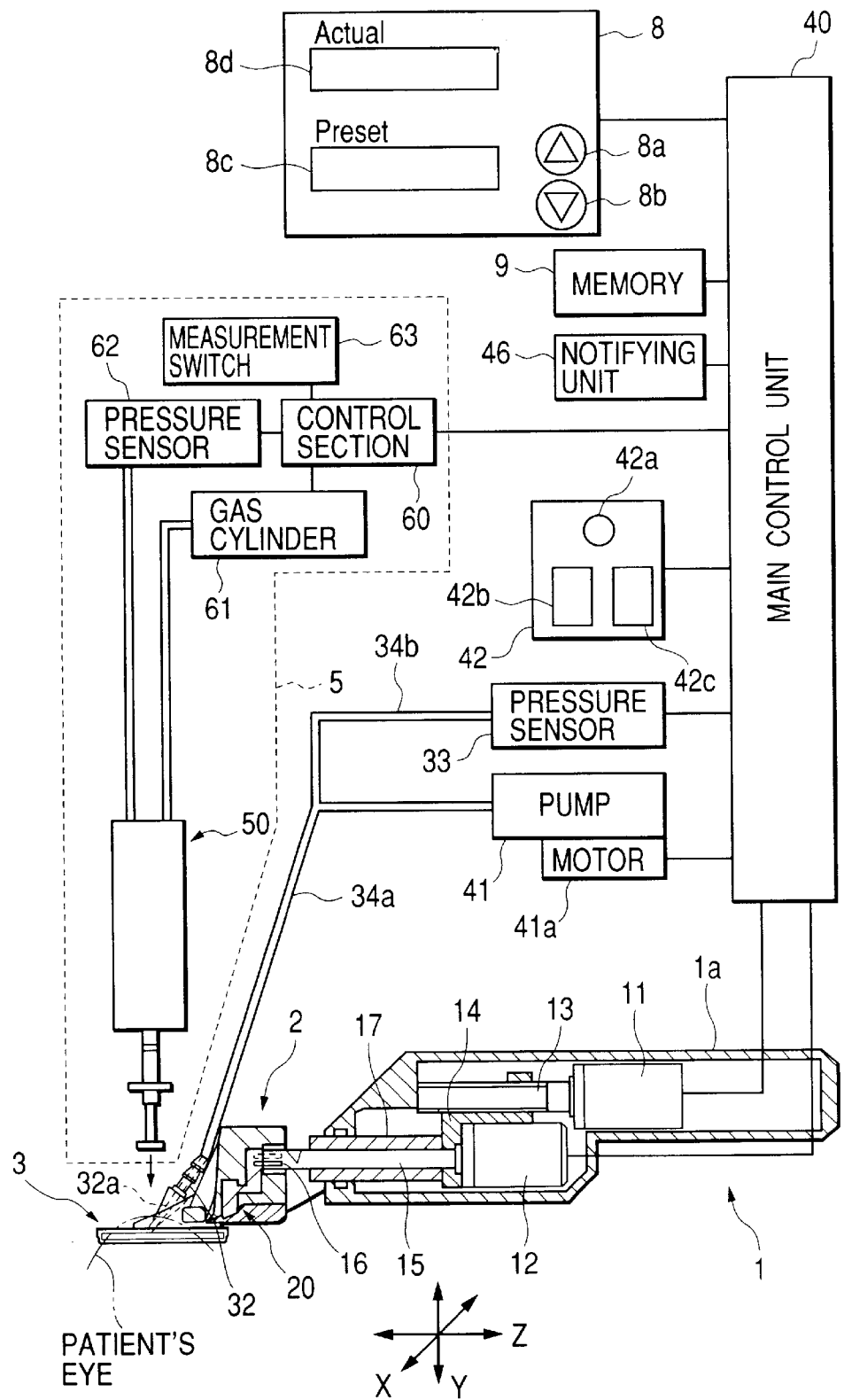
FIG. 1 is a cross-sectional view and a control system diagram of a corneal surgical apparatus in accordance with an embodiment of the present invention.

Referring to the accompanying drawings, a description will be given of an embodiment of the present invention. FIG. 1 is a cross-sectional view and a control system diagram of a corneal surgery apparatus in accordance with an embodiment of the present invention.

Reference numeral 1 denotes a main body of the corneal surgery apparatus (microkeratome), and reference numeral 1a denotes a grip to be held by an operator during the surgery. A suction unit 3 for fixing the apparatus to the patient's eye and a cutting unit 2, which has a blade 20 (which will be described later) for incising the cornea and is adapted to oscillate horizontally (laterally) and move in a forward linear direction (incising direction) on the suction unit 3, are provided on the front side (left-hand side in the drawing) of the main body 1.

A translating motor 11 for moving (translating) the cutting unit 2 in the incising direction (in the Z direction) and an oscillating motor 12 for imparting oscillations in the lateral direction (in the X direction) to the blade 20 are installed in the main body 1. A translating screw 13 is coupled to a rotating shaft of the motor 11, which has a threaded portion corresponding in length to the translation of the cutting unit 2. An attachment member 14 is engaged with threads to the screw 13. The motor 12 as well as a connecting member 17 for connecting the motor 12 and the cutting unit 2 are fixed to the attachment member 14. As the motor 11 rotating in a forward or reverse direction, the motor 12 and the connecting member 17 move forward or backward (in the Z direction) through the screw 13 and the attachment member 14, thereby causing the cutting unit 2 to move forward or backward (in the Z direction) Further, the connecting member 17 serves as a bearing or rotational support for a rotating shaft 15 so that the rotating shaft 15 is held by the connecting member 17. An eccentric pin 16 is embedded or protruded on a distal end of the rotating shaft 15 at a position offset from the center of rotation, and the eccentric shaft 16 imparts lateral oscillations to the blade 20 (which will be described later).

Figure 2:
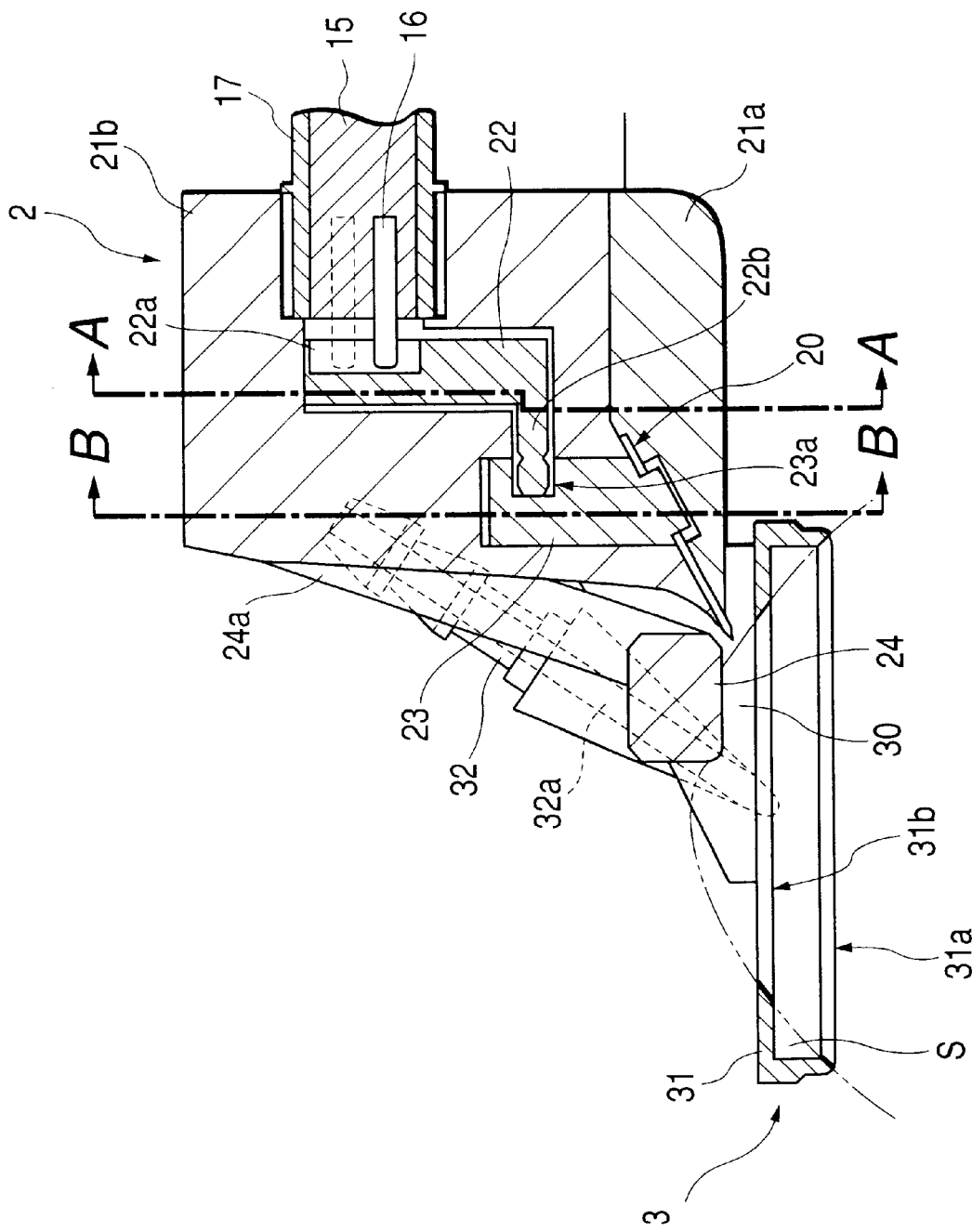
FIG. 2 is an enlarged explanatory diagram of a cutting unit and a suction unit of the apparatus.
Figure 3:
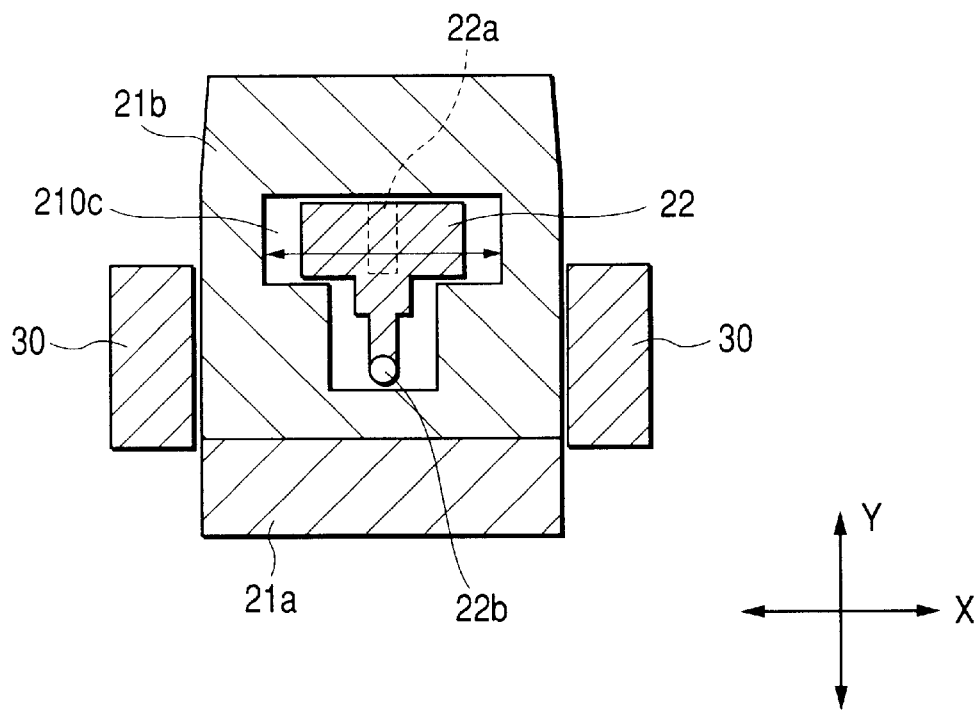
FIG. 3 is a cross-sectional view taken along line A—A of FIG. 2.
Figure 4:
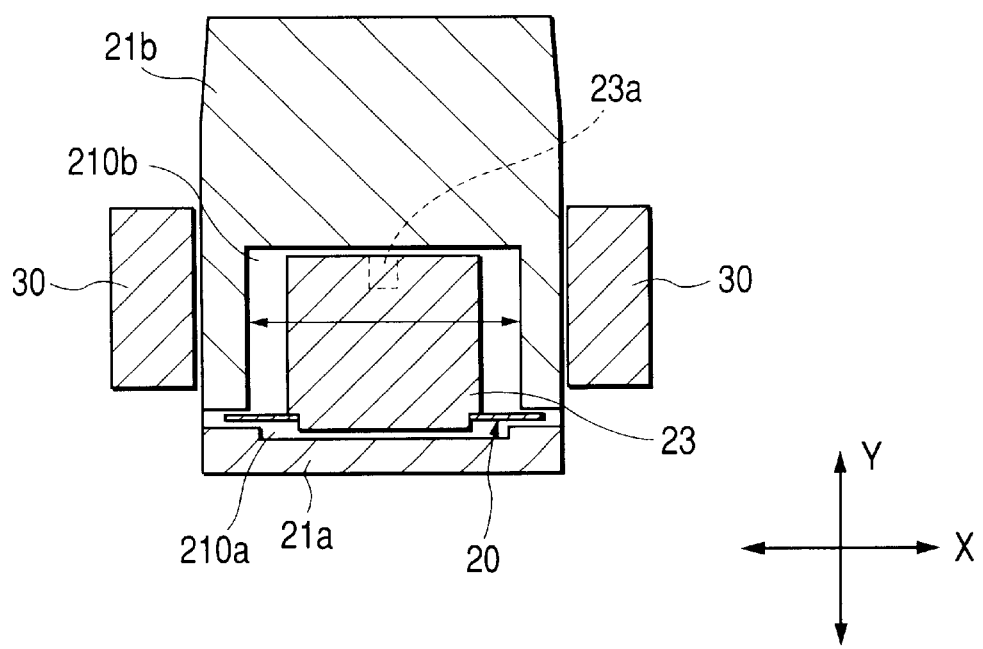
FIG. 4 is a cross-sectional view taken along line B—B of FIG. 2.

Referring next to FIGS. 2, 3 and 4, a description will be given of the arrangements of the cutting unit 2 and the suction unit 3. FIG. 2 is an enlarged view of the cutting unit 2 and the suction unit 3 shown in FIG. 1. FIG. 3 is a cross-sectional view taken along line A—A of FIG. 2. FIG. 4 is a cross-sectional view taken along line B—B of FIG. 2.

The cutting unit 2 is comprised of the blade 20 for corneal incision; a blade holder 21a and a holder block 21b for holding the blade 20 in such a manner as to permit lateral oscillations; a first oscillation transmitting member 22 for transmitting the lateral oscillations generated by the eccentric pin 16; a second oscillation transmitting member 23 for transmitting the lateral oscillations by the first transmitting member to the blade 20, and a cornea applanating member 24 fixed to the block 21b by means of an attachment member 24a. A rotation hole into which the rotating shaft 15 is inserted is provided inside the block 21b, and a tip portion of the connecting member 17 is fixed thereto.

A metal blade having a blade edge of stainless steel, steel, or the like or a mineral blade having a blade edge of diamond, sapphire or the like is used as the blade 20. The blade 20 is held between the holder 21a and the block 21b at an appropriate angle with respect to the horizontal plane in such a manner as to be capable of undergoing lateral oscillations. On the holder 21a side, a shallow recess 210a is formed at a portion where the blade 20 is placed, and the lateral width of the recess 210a is set to be larger than the oscillating width for the lateral oscillations of the blade 20.

The first transmitting member 22 is movable in the lateral direction (in the X direction) within a receiving groove 210c formed in the block 21b. The upper and lower portions of the first transmitting member 22 in the vertical direction (in the Y direction) is held by the block 21b. A vertical groove 22a for engagement with the eccentric pin 16 is formed in the first transmitting member 22. When the rotating shaft 15 is rotated by the rotative driving of the motor 12, the eccentric pin 16 engaged with the vertical groove 22a applies a lateral driving force to the first transmitting member 22. This causes the first transmitting member 22 to oscillate laterally.

The second transmitting member 23 is movable in the lateral direction (in the X direction) within the receiving groove 210b formed in the block 21b. The upper portion and the lower portion of the second transmitting member 23 are respectively held by the block 21b and the blade holder 21a. The first transmitting member 22 provides at its lower portion a protrusion 22b projected to the blade 20 side, and the second transmitting member 23 is formed with a vertical groove 23a engaged with the protrusion 22b. As the first transmitting member 22 is oscillated laterally by the rotation of the rotating shaft 15 (circumferential or circular motion of the eccentric pin 16), the protrusion 22b engaged with the vertical groove 23a is laterally oscillated, thereby applying lateral force to the second transmitting member 23. Accordingly, the second transmitting member 23 is laterally oscillated together with the blade 20 fixed to the second transmitting member 23.

The cornea applanating member 24 is provided on the front side (left-hand side in FIG. 2) of the blade 20 so as to applanate the cornea of the patient's eye in a flat manner in advance of the corneal incision by the blade 20 as the cutting unit 2 is moved forwardly. Since the blade 20 incises the cornea by first compressing the cornea flat with the applanating member 24, a flap of a uniform layer is formed.

In this embodiment, the distance between the edge of the blade 20 attached to the holder 21a and the lower surface of the applanating member 24 is set to be about 0.15 mm so that the cornea can be incised with this thickness in a layered fashion.

The suction unit 3 includes a fixing member 30, a suction ring 31, and a suction pipe 32. The suction ring 31 is fixed to the main body 1 by the fixing member 30. The suction ring 31 has a substantially hollow cylindrical shape (a substantially U-shape in section), which has a circular recessed portion 31a adapted to abut against the patient's eye, and an opening 31b concentric to the recessed portion 31a. When the suction ring 31 is mounted on the patient's eye for surgery, the cornea of the patient's eye projects upward through the opening 31b. The lower end portion of the suction ring 31 together with the opening end portion define a space S for suction.

The suction pipe 32 is connected to a vacuum tube 34a that extends to a pump 41 (see FIG. 1). A suction passage 32a provided inside the suction pipe 32 communicates with the recessed portion 31a. A vacuum is applied to the space S by the pump 41 through the passage 32a, the suction ring 31 is vacuum-fixed to the patient's eye. In this position, as the operator holds the main body 1, the opening 31b is accessible, and the entire apparatus can be held stably. When the suction ring 31 is vacuum-fixed to the patient's eye by the vacuum within the space S, the ocular pressure (ocular tension) of the patient's eye is increased, so that the cornea does not escape from and thus incised by the blade 20 even in a state where the cornea is applanated by the cornea applanating member 24.

Figure 9:
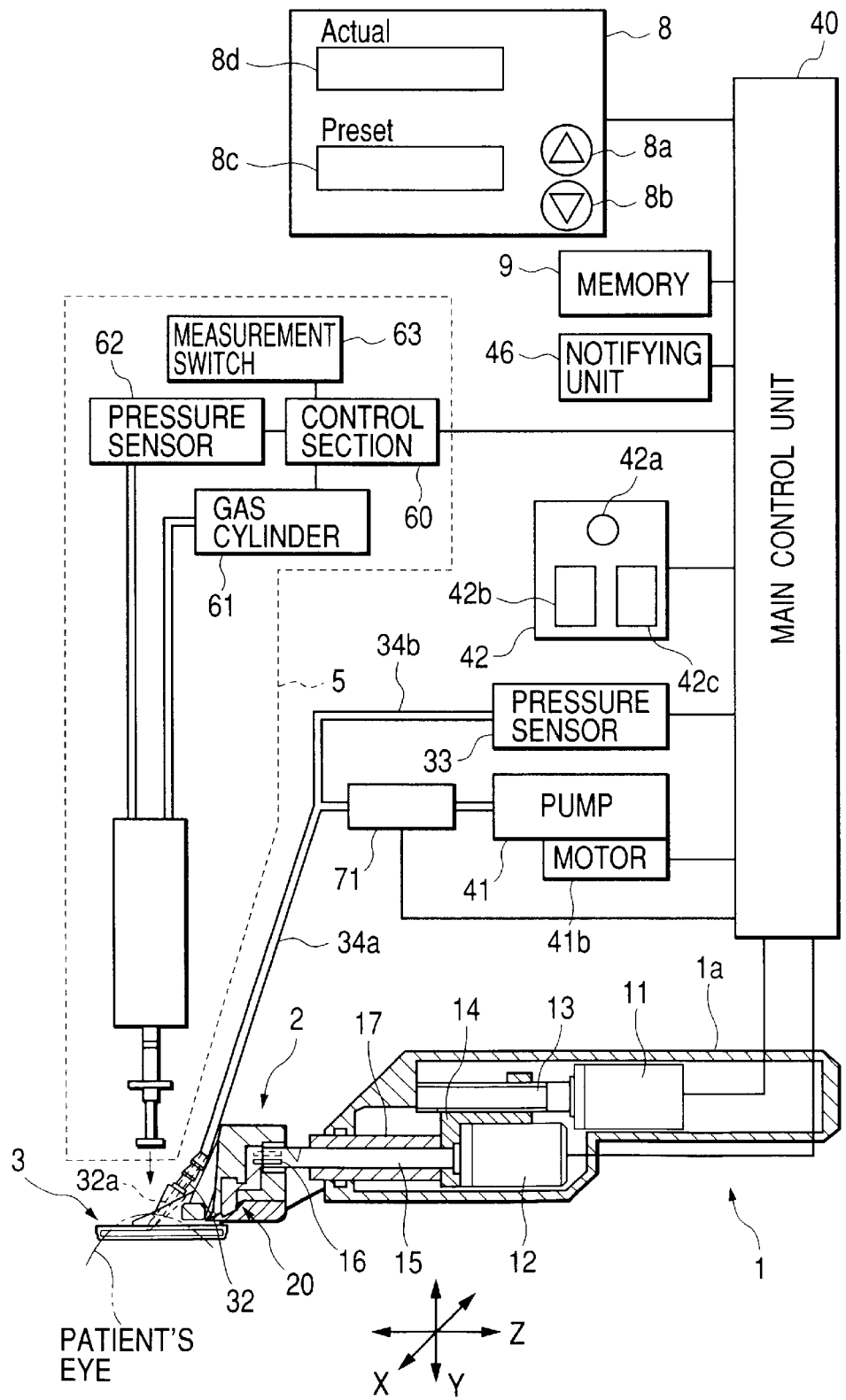
FIG. 9 is a diagram showing a modified example of the corneal surgical apparatus shown in FIG. 1.

The pump 41 has a rotational speed variable motor 41a as a power source, and accordingly can variably set the suction pressure (vacuum pressure) to an arbitrary value by changing the rotational speed of the motor 41a. The pump 41 may have, in place of the rotational speed variable motor 41a, a rotational speed fixed motor 41b as the power source, and an electromagnetic value mechanism 71 may be provided between the suction ring 31 and the pump 41 (in a portion of the tube 34a), so that the suction pressure can be variably set to a predetermined value by opening a release valve of the electromagnetic valve mechanism 71 (see FIG. 9).

A tube 34b is connected to a midway of the tube 34a, and to a pressure sensor 33. The pressure sensor 33 serves to detect the suction pressure (vacuum pressure) set by the pump 41.

Figure 5:
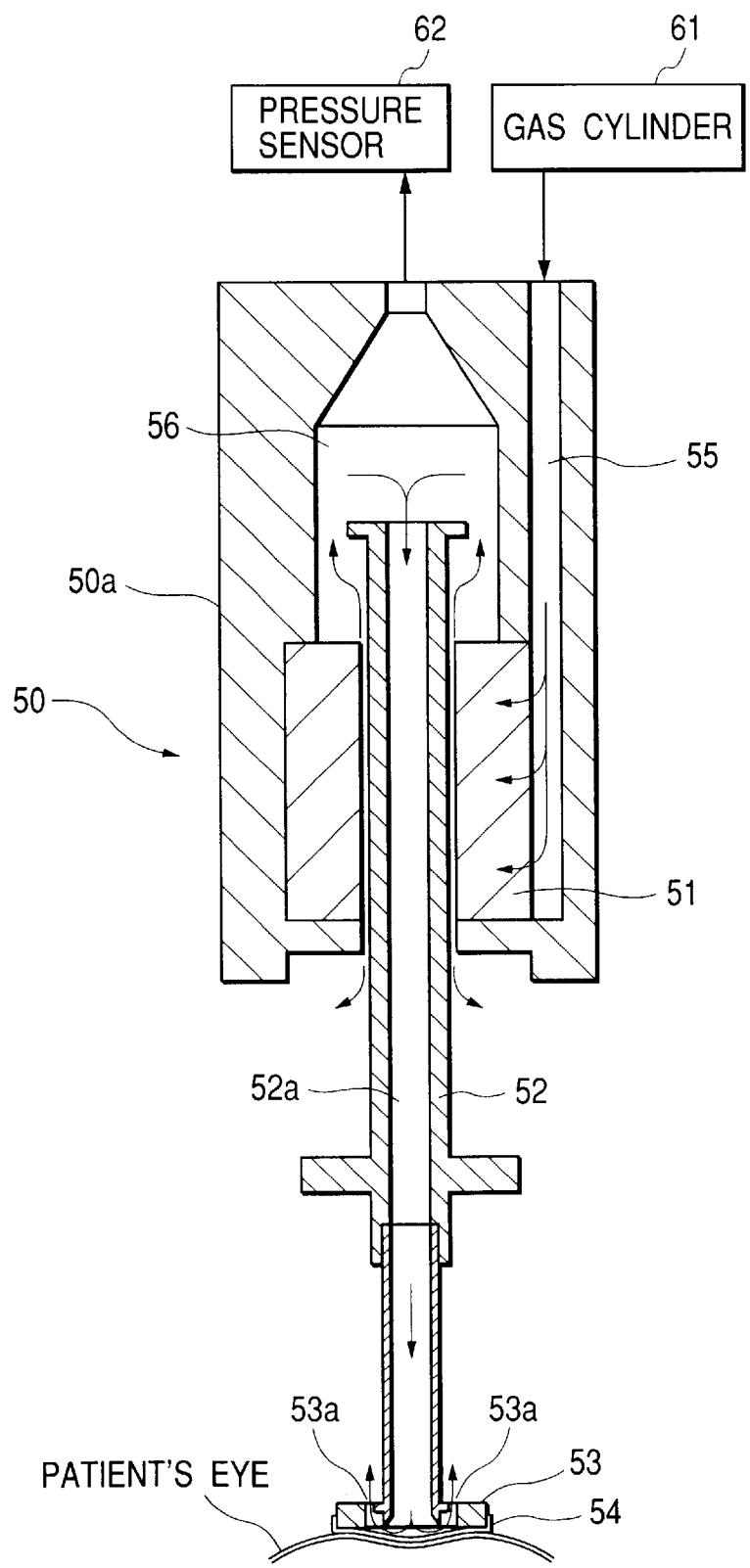
FIG. 5 is a cross-sectional view showing a general arrangement of an ocular pressure measuring unit.

In FIG. 1, reference numeral 5 designates an ocular pressure measuring unit for measuring the ocular pressure of a patient's eye. The ocular pressure measuring unit 5 in the embodiment shown in FIG. 1 employs a Pneumatic Applanation Tonometer, and is generally constructed as shown in FIG. 5. The Tonometer of this type is disclosed in U.S. Pat. No. 3,714,819, and therefore the reference should be made for the detailed construction thereof.

A probe 50 to be held by an operator includes a hollow piston 52, and a tip 53 mounted to a tip end of the piston 52. The piston 52 is supported to allow movement by a main body portion 50a. When Freon gas is allowed to flow at a predetermined rate from a gas cylinder 61 into a passage 55 formed in the main body portion 50a, part of the gas is supplied from a chamber 56, formed in the main body portion 50a, through a hollow portion 52a of the piston 52 to the tip 53. The rest of the gas is passed through an air bearing 51 to reduce the friction associated with the movement of the piston 52. A silicon rubber film 54 is stretched onto the end of the tip 53, so that when the rubber film 54 is brought into contact with the cornea, the rubber film 54 is convex toward the interior of the tip 53 to conform with the shape of the cornea (in this state, the flowing-out of the gas to the ambient air is suppressed). As the pressure in the chamber 56 is increased due to the flowing-in of the gas, the rubber film 54 gradually applanates the cornea, and when the balanced state is obtained, the gas is allowed to flow out to the ambient air through holes 53a. The chamber 56 communicates with a pressure sensor 62, and the pressure sensor 62 detects the pressure within the chamber 56 at the balanced state. The pressure sensor 62 is connected to a control section 60, and the control section 60 calculates the ocular pressure based on an output signal of the pressure sensor 62.

The data on ocular pressure, obtained by the control section 60 of the ocular pressure measuring unit 5, are inputted into a main control unit 40 for controlling the main body 1 side in accordance with an instruction from the control section 60. Connected to the control unit 40 are: the control section 60; an operation panel 8 for setting an ocular pressure value, etc. during surgery, a memory 9 for storing data; a notifying unit 46 for generating an alarm sound, a foot switch 42 (including a switch 42a for turning on and off the pump 41, a switch 42b for starting the translating motion and oscillating motion of the blade 20, and a switch 42c for returning the cutting unit 2), the pump 41, and the pressure sensor 33.

Hereafter, a description will be given of the operation of the apparatus having the above-described configuration. Prior to the surgery, the operator sets a desired occular pressure value for incision of the cornea using an UP bottom 8a and/or a DOWN bottom 8b on the operation panel 8. The value thus set is displayed on a preset display portion 8c. (The value may be preliminarily set as a standard set value for the apparatus.)

While confirming the orientation of the suction ring 31 (main body 1) to the position of the pupillary center, and a mark that has been preliminarily applied on the patient's cornea using an instrument such as a marker, the operator aligns the center of the opening 31b with the pupillary center, and applies the suction ring 31 on the patient's eye. The tip 53 of the probe 50 is applied to the cornea, and a measurement switch 63 (preferably, in the form of a foot switch) is depressed to establish a stand-by state of the ocular pressure measurement.

After installation of the suction ring 31, the operator, while keeping the position and the posture of the main body 1, steps on (depresses) the switch 42a of the foot switch 42 to operate the pump 41 to thereby apply vacuum into the space S between the suction ring 31 and the patient's eye and produce suction. The operator brings the tip 53 (the rubber film 54) into light contact with the corneal surface to measure the ocular pressure of the patient's eye. The ocular pressure data, obtained sequentially (in time relation) and continuously (or intermittently at a predetermined sampling interval) by the control section 60 of the occular pressure measuring unit 5, are inputted to the main control unit 40, so that the varying ocular pressure value is displayed on the measured ocular pressure display portion 8d of the operation panel 8.

If the air pressure in the space S between the patient's eye and the suction ring 31 is decreased, the ocular pressure of the patient's eye is increased accordingly. The ocular pressure data, inputted sequentially (in time relation) and continuously (or intermittently) from the control section 60 are monitored by the main control unit 40. The main control unit 40 controls the driving of the pump 41 (the motor 41a) so that a pressure value indicated by the monitored occular pressure data is coincident with the set occular value (falls within a predetermined tolerable range). The main control unit 40 may directly obtain an output signal of the pressure sensor 62 of the ocular pressure measuring unit 5 to control the driving of the pump 41 based on a relation ship between the thus obtained output signal and the set ocular pressure value. In case the electromagnetic value mechanism 71 is provided between the suction ring 31 and the pump 41, the main control unit 40 adjusts and controls the leakage amount of a release valve of the mechanism 71.

The suction pressure in the space S, which is detected by the pressure sensor 33 at the time when the monitored pressure reaches the set ocular pressure value, is stored in the memory 9. The main control unit 40 controls the driving of the pump 41 while monitoring the suction pressure detected by the pressure sensor 33, in order to maintain the suction pressure at the thus stored suction pressure during the incising surgery. Of course, the incising surgery can be conducted while monitoring the ocular pressure data sequentially (in time relation) and continuously (or intermittently) inputted from the control section 60.

The main control unit 40, when the set ocular pressure is reached, notifies through the notifying unit 46 to the operator that the set ocular pressure is obtained. The operator, after confirming that the set ocular pressure is obtained, removes the probe 50 from the cornea, and starts the corneal incision.

The operator operates the switch 42b of the foot switch 42 to rotatively drive the motor 11 and the motor 12. Upon reception of the drive instruction signal from the switch 42b, the main control unit 40 controls the rotational driving of the motor 12 so that the blade 20 is oscillated laterally. Concurrently, the control unit 40 controls the rotational driving of the motor 11 so that the cutting unit 2 is moved toward the hinge (in the incise direction) . Accordingly, the rotating shaft 15 slides in the advancing direction integrally with the cutting unit 2 while making rotational motion for imparting lateral oscillations to the blade 20.

By sliding of the blade 20, an upper part of the cornea is incised to form a flap. The thickness of the flap is determined by the clearance between the edge of the blade 20 and the lower surface of the cornea applanating member 24, but varied depending on the fluctuation of the ocular pressure. In general, as the ocular pressure is higher, the flap thickness is larger, and as the ocular pressure is lower, the flap thickness is smaller. In the apparatus of the present embodiment, the main control unit 40 controls the air pressure in the space S (the suction pressure applied to the space S) during surgery so as to maintain the ocular pressure at the ocular pressure value set preliminarily. Therefore, an appropriate flap intended by the operator can be obtained stably.

When the flap formation is complete, that is, the edge of the blade 20 has incised the cornea with the hinge portion left, the switch 42c is depressed to rotate the motor 11 in the reverse direction to return the cutting unit 2 to its initial position. For this return operation, the rotation of the motor 12 is stopped using the independent control of the motors 11 and 12, to thereby withdraw or remove the blade 20 from the flap while avoiding the unnecessary oscillation of the blade 20.

After the cutting unit 2 is returned to its initial position, the driving of the pump 41 is stopped, and the air is introduced into the space S to release the suction of the suction ring 31, and the apparatus (the suction ring 31) is removed. Subsequently, a refractive correction amount of the corneal stroma is ablated and removed using excimer laser light, and then the flap is returned to its original position, thereby completing the surgery.

Although the embodiment has been described by taking an example in which the Pneumatic Applanation Tonometer is used to obtain the ocular pressure sequentially (in time relation) and continuously (or intermittently), the present invention should not be limited thereto and can employ various types of ocular pressure measuring units. For example, the present invention can be constructed by using an ocular pressure measuring unit of a type in which the cornea is depressed by an applanating member, and an ocular pressure is measured, as desired, based on a depressing force that is applied by the applanating member when the cornea is put into a desired applanating state.

Figure 6:
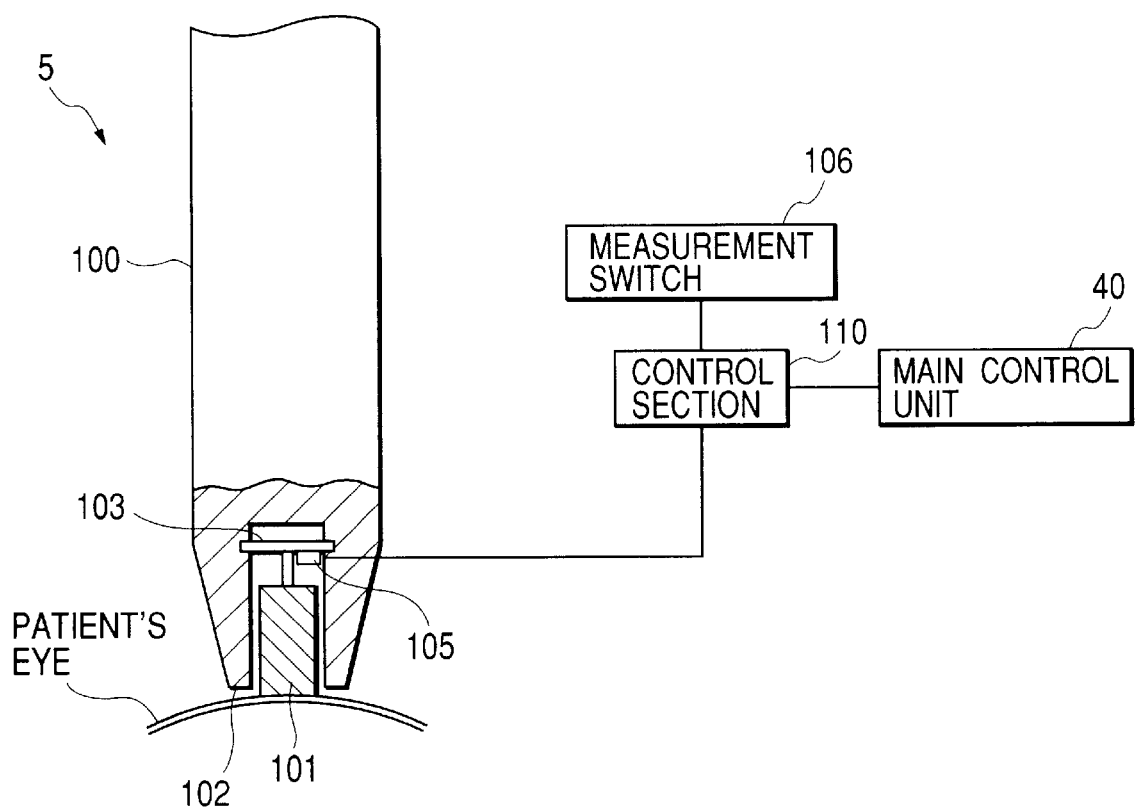
FIG. 6 is a partially, cross-sectional view showing a general arrangement of another ocular pressure measuring unit.

FIG. 6 is a diagram showing a general arrangement of an ocular pressure measuring unit 5' which constitutes such a modified example. A contact guide 102 is formed at a tip end of a probe 100, and an applanating member 101 for applanating the cornea is provided at a central portion of the contact guide 102. To measure the ocular pressure, the tip end surface of the applanating member 101 and the tip end surface of the contact guide 102 are both brought into contact with the cornea. A strain plate 103 is fixed to a rear portion of the applanating member 101, and an output of a strain gage 105 on the strain plate 103 is inputted to a control section 110. The control section 110 obtains a depressing force applied by the applanating member 101 based on the output of the strain gage 105, to calculate the ocular pressure. Reference numeral 106 designates a measurement switch.

Figure 7:
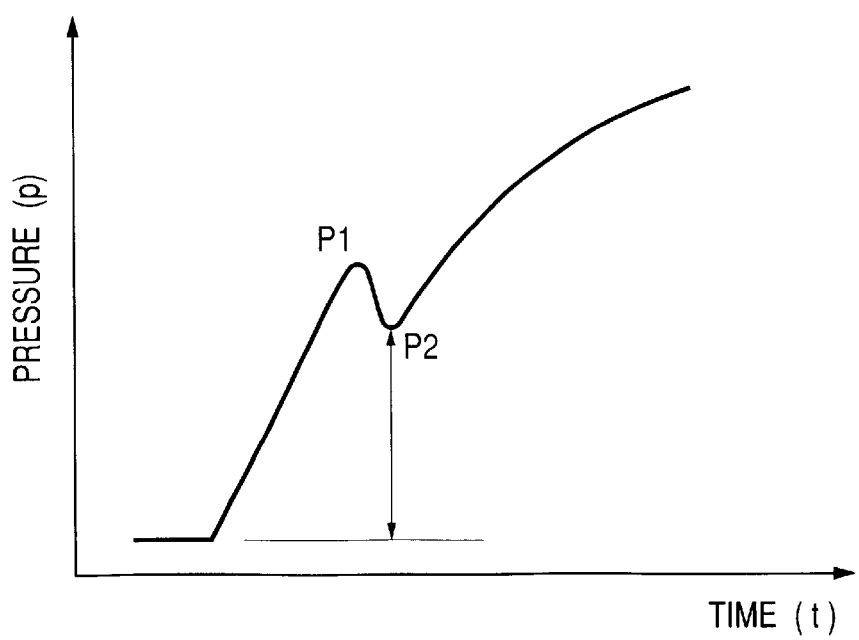
FIG. 7 is an explanatory diagram for explaining a measuring principle of the ocular pressure measuring unit shown in FIG. 6.

This ocular pressure measuring unit 5' utilizes a measuring principle of a Mackay-Marg Tonometer (see, for example, U.S. Pat. No. 4,747,296), and the measuring principle of the unit 5' is briefly discussed with reference to FIG. 7. As the spherical cornea is applanated in a flat manner by the applanating member 101 gradually, the force acting on the applanating member 101 is increased up to a point P1 where an applanating area of the cornea is equal to a contact area with the applanating member 101. As the cornea is further applanated flatly so that the applanating area of the cornea is beyond the contact area with the applanating member 101, the cornea is brought into contact with the contact guide 102 around the applanating member 101. Accordingly, the force due to the rigidity of the cornea is dispersed to the contact guide 102 and thus the force acting on the applanating member 101 is decreased. (Therefore, a pressure drop occurs as shown in FIG. 7 representing a relationship of an applanating amount to a force.) The lowest point P2 of this pressure drop can be considered such that the force due to the rigidity of the cornea is completely dispersed to the base (contact guide 12), and therefore, the pressure value at the lowest point P2 is converted into the ocular pressure.

The ocular pressure measuring unit 5' thus constructed does not measure the ocular pressure of the patient's eye sequentially (in time relation) and continuously (or intermittently). For this reason, the main control unit 40 controls the driving of the pump 41 in the following manner to maintain the ocular pressure at the preliminarily set ocular pressure value.

The ocular pressure, which is being increased due to the driving of the pump 41, is measured several times (at the times of different suction pressures) using the ocular pressure measuring unit 5'. The main control unit 40 stores ocular pressure data obtained at each measurement and suction pressure data obtained by the pressure sensor 33 at a time point at which the ocular pressure data are obtained, into the memory 9 so that these data are related to each other to form a set.

Figure 8A:
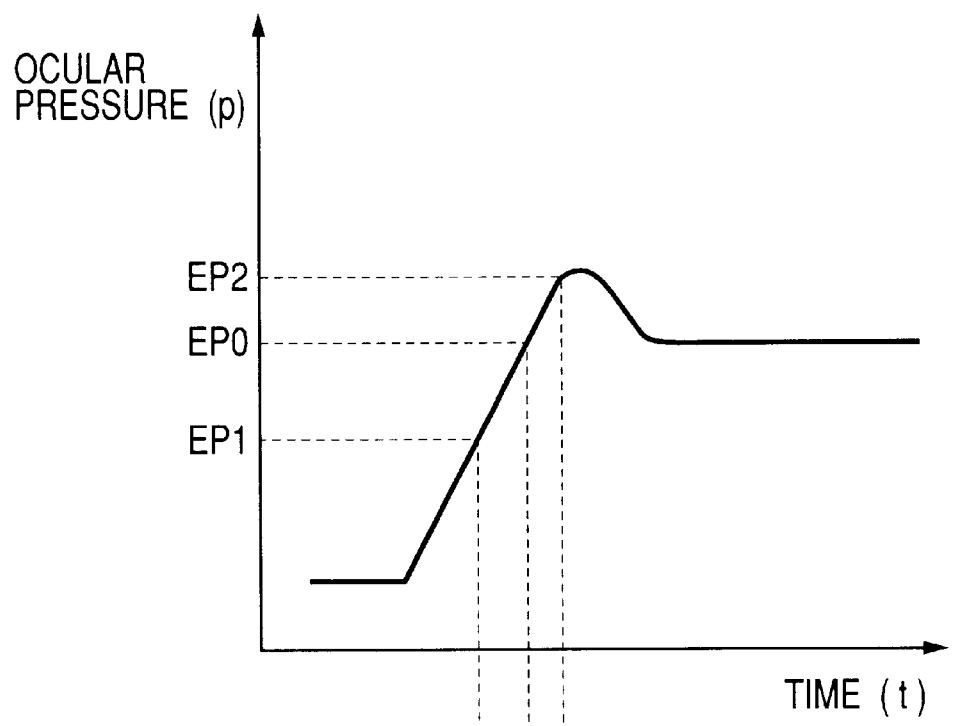
FIG. 8 is an explanatory diagram for comparison between fluctuation of ocular pressure and fluctuation of suction pressure.
Figure 8B:
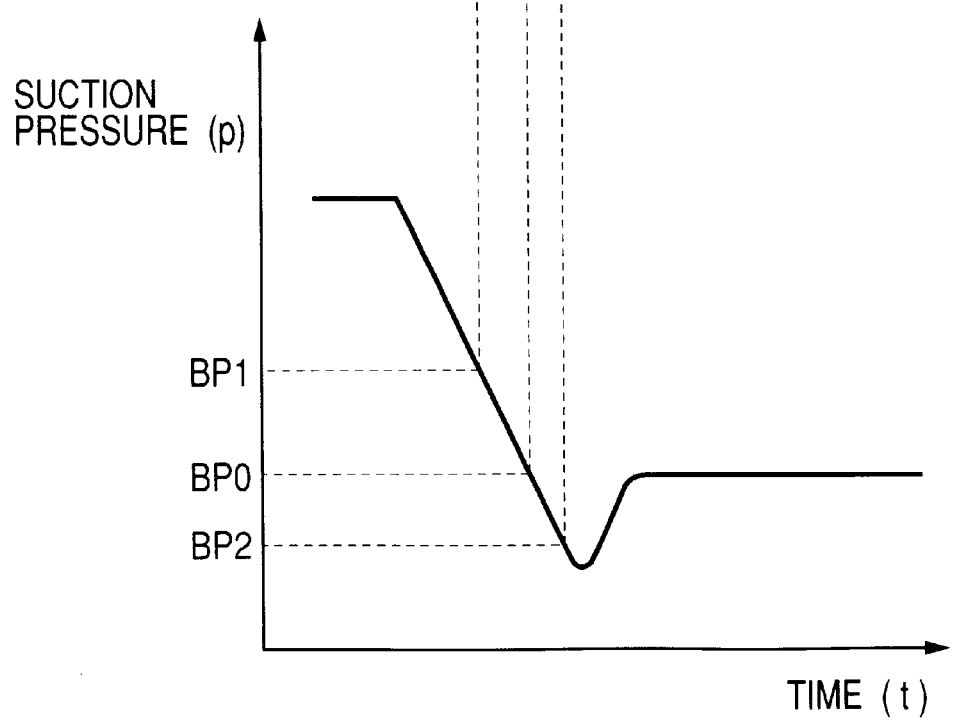

As shown in FIG. 8, if at least two sets of data, one set being a measured ocular pressure value EP1 lower than the set ocular pressure EP0 and a suction pressure BP1 at this time point, and the other set being a measured ocular pressure EP2 higher than the set ocular pressure value EP0 and a suction pressure BP2 at this time point, are obtained, then a suction pressure BP0 making the ocular pressure identical to the set ocular pressure EP0 can be obtained based on ratios of EP1 and EP2 with respect of EP0. Subsequently, the main control unit 40 controls the driving of the pump 41 while monitoring the suction pressure detected by the pressure sensor 33 so that the monitored suction pressure reaches the thus obtained suction pressure BP0.

The suction pressure BP0 is stored in the memory 9, and the main control unit 40 controls the driving of the pump 41 (the motor 41a) while monitoring the suction pressure detected by the pressure sensor 33 so that the monitored suction pressure is maintained at the stored suction pressure BP0 during the incising surgery. When the suction pressure BP0 is first detected by the sensor 33, the main control unit 40 notifies the operator of this condition through the notifying unit 46. This makes it possible to carry out the incising surgery with the suction pressure kept at the desired ocular pressure similarly to the former example.

In case of the ocular pressure measurement using the ocular pressure measuring unit of this type, the ocular pressure at the suction pressure BP0 obtained by the main control unit 40 may be measured again. If the measured ocular pressure vale is out of a tolerable range of the set occular pressure value, the suction pressure may be corrected taking into account the result of measurement.

Although the corneal surgical apparatus using the blade translating mechanism for moving the blade in the forward linear direction (the incise direction) while oscillating the blade laterally has been described, the corneal surgical apparatus is not limited to have the blade translating mechanism of this type. For example, the blade translating mechanism for the corneal surgical apparatus of the present invention may be designed to move the blade in the circular locus (path), or may have any other forms.

As described above, according to the present invention, a consistent flap of appropriate thickness can be formed.

What is claimed is:

1. A corneal surgical apparatus comprising;
   a suction ring to be mounted on a patient's eye;
   a suction unit which applies a suction pressure to a space defined between the patient's eye and the mounted suction ring;
   a setting unit which sets a desired ocular pressure for the patient's eye;
   an input unit which inputs a measured ocular pressure of the patient's eye; and
   a controller which controls the suction pressure to be applied by the suction unit based on comparison between the inputted ocular pressure and the set ocular pressure.

2. The corneal surgical apparatus of claim 1, wherein:
   the input unit inputs the measured ocular pressure sequentially; and
   the controller controls the suction pressure to be applied by the suction unit while monitoring the sequentially inputted ocular pressure so that the inputted ocular pressure is identical to the set ocular pressure.

3. The corneal surgical apparatus of claim 1, further comprising:
   an ocular pressure measuring unit which measures the ocular pressure of the patient's eye,
   wherein the input unit inputs the ocular pressure measured by the ocular pressure measuring unit.

4. The corneal surgical apparatus of claim 1, wherein:
   the suction unit includes a pump having a motor as a power source; and
   the controller controls a rotational speed of the motor.

5. The corneal surgical apparatus of claim 1, wherein:
   the suction unit includes a pump, a suction tube connected to the pump and a valve mechanism provided to the suction tube; and
   the controller controls a leakage amount of the valve mechanism.

6. The corneal surgical apparatus of claim 1, further comprising:
   a cutting unit which is provided with a blade movable along the suction ring.

7. A corneal surgical apparatus comprising:
   a suction ring to be mounted on a patient's eye;
   a suction unit which applies a suction pressure to a space defined between the patient's eye and the mounted suction ring;
   a setting unit which sets a desired ocular pressure for the patient's eye;
   an input unit which inputs a measured ocular pressure of the patient's eye;
   a pressure sensor which detects the suction pressure applied by the suction unit;
   a memory which stores the suction pressure detected when the inputted ocular pressure is identical to the set ocular pressure; and
   a controller which controls the suction pressure to be applied by the suction unit based on comparison between detected suction pressure and the stored suction pressure.

8. The corneal surgical apparatus of claim 7, wherein:
   the pressure sensor detects the suction pressure sequentially; and
   the controller controls the suction pressure to be applied by the suction unit while monitoring the sequentially detected suction pressure so that the detected suction pressure is identical to the stored suction pressure.

9. The corneal surgical apparatus of claim 7, further comprising:
   an ocular pressure measuring unit which measures the ocular pressure of the patient's eye,
   wherein the input unit inputs the ocular pressure measured by the ocular pressure measuring unit.

10. A corneal surgical apparatus comprising:
    a suction ring to be mounted on a patient's eye;
    a suction unit which applies a suction pressure to a space defined between the patient's eye and the mounted suction ring;
    a setting unit which sets a desired ocular pressure for the patient's eye;
    an input unit which inputs a measured ocular pressure of the patient's eye;
    a pressure sensor which detects the suction pressure applied by the suction unit;
    a memory which stores a plurality of the inputted ocular pressures measured when different suction pressures are applied, and the detected suction pressures when those ocular pressures are respectively measured, in relation to each other; and
    a controller which calculates the suction pressure corresponding to the set ocular pressure based on plural sets of the ocular pressures and suction pressures stored in the memory, stores the calculated suction pressure in the memory, and controls the suction pressure to be applied by the suction unit based on comparison between detected suction pressure and the calculated and stored suction pressure.

11. The corneal surgical apparatus of claim 10, wherein:
    the pressure sensor detects the suction pressure sequentially; and
    the controller controls the suction pressure to be applied by the suction unit while monitoring the sequentially detected suction pressure so that the detected suction pressure is identical to the calculated and stored suction pressure.

12. The corneal surgical apparatus of claim 10, further comprising:
    an ocular pressure measuring unit which measures the ocular pressure of the patient's eye,
    wherein the input unit inputs the ocular pressure measured by the ocular pressure measuring unit.

* * * * *